United States Patent
Villanueva Decodes (10) Patent No.: US 11,633,512 B2
(45) Date of Patent: Apr. 25, 2023

(54) METHOD FOR DISINFECTING SOILS OR OTHER AGRICULTURAL GROWING MEDIA

(71) Applicant: Agrozono, S.L., Valencia (ES)

(72) Inventor: Emilio Jesús Villanueva Decodes, Valencia (ES)

(73) Assignee: Agrozono, S.L., Valencia (ES)

( * ) Notice: Subject to any disclaimer, the term of this patent is extended or adjusted under 35 U.S.C. 154(b) by 384 days.

(21) Appl. No.: 16/628,843

(22) PCT Filed: Jul. 6, 2017

(86) PCT No.: PCT/ES2017/070488
§ 371 (c)(1),
(2) Date: Jan. 6, 2020

(87) PCT Pub. No.: WO2019/008195
PCT Pub. Date: Jan. 10, 2019

(65) Prior Publication Data
US 2020/0197553 A1   Jun. 25, 2020

(51) Int. Cl.
*A61L 2/18*  (2006.01)
*B09C 1/02*  (2006.01)
(Continued)

(52) U.S. Cl.
CPC ............... *A61L 2/183* (2013.01); *B09C 1/02* (2013.01); *B09C 1/10* (2013.01); *C05F 11/08* (2013.01); *C09K 17/40* (2013.01); *B09C 2101/00* (2013.01)

(58) Field of Classification Search
None
See application file for complete search history.

(56) References Cited

U.S. PATENT DOCUMENTS 5,951,978 A * 9/1999 Red'kina ............... C12N 1/205
                                                    435/252.4
6,893,565 B2 * 5/2005 Greene ..................... C02F 9/00
                                                    210/602
(Continued)

FOREIGN PATENT DOCUMENTS

CN       102640668 A        8/2012
CN       102668952     *    9/2012   ............. Y02P 60/21
(Continued)

OTHER PUBLICATIONS

Argozono, Oct. 14, 2016, 4 pages, https://web.archive.org/web/20161014180145/https:/agrozono.net/procedimiento-de-aplicacion/.
(Continued)

*Primary Examiner* — Wayne A Langel
(74) *Attorney, Agent, or Firm* — The Webb Law Firm (57) ABSTRACT

The invention relates to a method for disinfecting soils or other agricultural growing media, characterised by comprising the following steps: obtaining a soil or other agricultural growing medium at their field capacity; treating the soil or medium at the field capacity of the previous step with ozonated water, wherein the ozonated water is prepared in situ with ozone-production equipment connected to the water supply; allowing a period of time to pass after the treatment with ozone; and inoculating the disinfected soil or agricultural medium with at least one species of beneficial microorganism.

11 Claims, 9 Drawing Sheets

(51) Int. Cl.
*B09C 1/10* (2006.01)
*C05F 11/08* (2006.01)
*C09K 17/40* (2006.01)

(56) References Cited

U.S. PATENT DOCUMENTS

| | | | | |
|---|---|---|---|---|
| 7,651,615 | B2 * | 1/2010 | Greene | C12P 7/08 |
| | | | | 210/627 |
| 2016/0145163 | A1 * | 5/2016 | Wallenstein | C05F 11/08 |
| | | | | 71/6 |

FOREIGN PATENT DOCUMENTS

| | | | | | |
|---|---|---|---|---|---|
| CN | 203486954 | U | * | 3/2014 | C02F 1/68 |
| CN | 104094786 | A | * | 10/2014 | A01G 9/02 |
| CN | 205234998 | U | * | 5/2016 | A61L 2/18 |
| ES | 2625034 | A1 | | 7/2017 | |
| JP | H1030091 | A | | 2/1998 | |
| JP | 200220211 | A | | 1/2002 | |
| KR | 100771050 | B1 | * | 10/2007 | B09C 1/08 |
| KR | 101630824 | B1 | * | 6/2016 | C05F 11/00 |
| KR | 20170015775 | A | * | 2/2017 | C05F 3/00 |

OTHER PUBLICATIONS

Fujiwara et al., "Effects of Ozonated Water Application on the Population Density of *Fusarium oxysporum* f. sp *ycopersici* in Soil Columns", Ozone: Science and Engineering, Apr. 2006, pp. 125-127, vol. 28.

* cited by examiner

METHOD FOR DISINFECTING SOILS OR OTHER AGRICULTURAL GROWING MEDIA

CROSS-REFERENCE TO RELATED APPLICATION

This application is the United States national phase of International Application No. PCT/ES2017/070488 filed Jul. 6, 2017, the disclosure of which is hereby incorporated by reference in its entirety.

BACKGROUND OF THE INVENTION

Field of the Disclosure

The present patent application describes a method for disinfecting soils and other agricultural growing media by using ozone, in particular ozonated water generated in the place and time of application.

Description of Realted Art

Climate change, increases in population, and the imminent scarceness of natural resources, make it necessary to change the traditional agricultural production models and substitute them with more sustainable production systems.

Moreover, since 1840, it has been known that ozone is the most powerful oxidant that exists. Additionally, its efficiency as a germicidal and bactericidal agent has also been demonstrated with several studies. In agriculture, it has been demonstrated that ozone has additional benefits, both for the crop and the grower, such as: greater growth for the plants, lesser ripening time for the fruit, higher production and taste, and less risk of disease.

Until a short time ago, the use of Methyl bromide was allowed, a compound which is very effective and widely known. Since it was prohibited, other registered chemical products are being used such as Chloropicrin, 1-3 Dichloropropene or a mixture of both (Agrocelhone), Metam-sodium, Metam-potassium, Methyl thioisocyanate. However, all these products must be handled by accredited personnel according to RD 1311/2012, since they are dangerous for people and the environment, and especially surface and underground water, and the safety period for planting is greater than one month, the soil needing to be kept non-productive during that time.

Moreover, the disinfection methods used until now in agriculture use chemical additives that create residues. This is not the case in the use of ozone to disinfect soils or media for agricultural use and, therefore, it is not necessary to establish a waiting period until cultivation.

However, the instability of the ozone in the medium makes it so that it cannot be stored and that it must be produced on demand at the application site, which requires a high energy demand, which is a significant drawback. For this reason, until now, methods are not known which enable an effective disinfection of the soil using ozone.

The artificial generation of ozone is generally performed by activating the oxygen from the air by means of high-voltage electrical discharges. This electrical energy breaks the oxygen molecule, recombining the atoms thereof to form OZONE. Nature does this in the same manner in storms.

Releasing energy when generating ozone is an endothermic process, the energy of which comes from the electrical discharge. In the same manner, the ozone spontaneously decomposes into diatomic oxygen, releasing the excess energy, for which reason it must be generated at the time and place of immediate use. To do so, equipment called "ozonisers" or ozone generators are used.

Since the end of the 19th century, the disinfecting and antiseptic properties of ozone have been studied and since then it has been used with high effectiveness in environmental treatments. Its capacity to break molecules with a double bond and aromatic rings, by means of the mechanism called ozonolysis, makes ozone have many applications, among which, as a bactericide, virucide, fungicide and deodorant; quickly destroying streptococci, staphylococci, colibacteria, etc., as well as the most energetic diphtheria and tetanus toxins.

Generally, ozone is used to perform one or more of the following fundamental functions: microbicide, deodorant and oxygenating agent. Among these, the microbicidal activity is perhaps the most important quality of ozone. Due to the oxidising properties thereof, ozone can be considered as one of the quickest and most effective microbicidal agents known. The action thereof has a wide spectrum which encompasses the elimination of bacteria, fungi, viruses and nematodes.

Additionally, ozone is often used for the deodorant activity thereof, being very useful in all kinds of public venues and in the treatment of certain odours of industrial origin, human smells, moisture, tobacco, food, etc. On the one hand, ozone oxidises the organic matter (ozonolysis) and, on the other hand, it attacks the microbes that feed on it. There is a wide range of smells that can be attacked by ozone.

In large cities, where there is a large amount of closed and poorly-ventilated venues, the depletion of air is frequently noticeable as a consequence of a lack of oxygen, which we normally identify as stale air. Ozone, due to the high oxygen-providing power it has, contributes to improving the efficiency of the cells of advanced organisms as far as taking advantage of the available oxygen, by means of the stimulation of several enzymes which intervene in these processes. Furthermore, the decomposition of the ozone must necessarily be into oxygen, which will be located there where the ozone gas has penetrated, in the air, in the water, or underground.

As mentioned earlier, the disinfecting action of the ozone is produced by oxidation. In low pH conditions due to molecular oxidation and high pH media due to oxidation by means of hydroxyls. Due to these oxidising properties, ozone is considered as one of the quickest and most effective microbicidal agents known.

As an alternative method to the use of ozone, in the state of the art disinfection methods based on the use of chlorine are also known. In processes of this type, the disinfecting action is produced when the chlorine extends along the cell walls and oxidises the enzyme and, consequently, they are slow disinfection methods. However, the ozone-based disinfection methods are advantageous, since in these methods the cellular membranes are destroyed or decomposed in a very fast process wherein, as an additional advantage, the ozone is deactivated by transforming into oxygen. More specifically, the ozone acts on the cell wall of the microorganism by degrading it which creates a "hole" through which it loses the cellular fluid thereof. Disinfection by ozone is called bacteriolysis.

Additionally, ozone-based treatments require a residual dose of disinfectant and an application period which is significantly shorter than in disinfection methods based on chemical additives such as chlorine. Thus, in general, a residual dose of ozone of 0.1 mg/l for 5 seconds is necessary, compared to the 4 hours necessary for chlorine. It has also been determined that ppm of ozone are needed for four minutes in order to eliminate microorganisms. Ozone can also kill 99% of 60,000 coliform bacteria/ml in water contaminated in 2.8 seconds with a dose of ppm, with the same dose of chlorine 15,000 seconds are needed.

Another significant advantage of using ozone in the elimination of microorganisms is that resistances are not developed due the fact that the action mechanism thereof is based on the rupture of the cell wall. Generally, aerobic spore-forming bacteria are disinfected more easily than anaerobic spore-forming bacteria. The effectiveness of the disinfection in solution is higher compared to the bacteria from the lactic acid and, therefore, also compared to the yeast of fungi.

Figure 1:
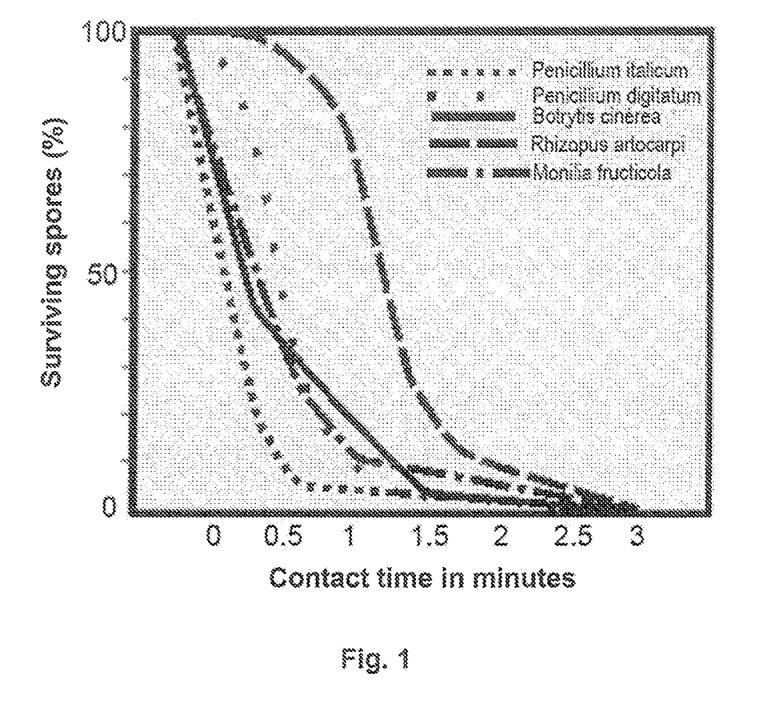
FIG. 1: Diagram showing the effect of water with ozone on several fungi.

In FIG. 1, we can see the time needed for the pathogen to be in contact with the ozone, whether in air or mixed with water, in order to be destroyed.

As mentioned earlier, the disinfectant properties of ozone are widely known. Furthermore, methods for disinfecting air or water using this compound are also known. However, although on occasion water disinfected with ozone has been used as irrigation water, until now an effective method is not known for disinfecting soils and other agricultural growing media using ozone as a disinfectant.

DESCRIPTION

In a first aspect, the present patent application relates to a method for disinfecting soils or other agricultural growing media, characterised by comprising the following steps:
  obtaining a soil or other agricultural growing medium at their field capacity;
  treating the soil or medium at the field capacity of the previous step with ozonated water containing at least 2 ppm of ozone, preferably between 5 to 6 ppm of ozone, wherein the ozonated water is prepared in situ with ozone-production equipment connected to the water supply with a pH between 5.0 and 7.5, preferably the water has a pH between 5.0 and 7.0;
  allowing a minimum period of 30 min to pass, preferably between 30 min and 48 hours, from the treatment with ozone; and
  inoculating the disinfected soil or agricultural medium with at least one species of beneficial microorganism.

Preferably, the ozone treatment is applied for between 1 h 30 min and 2 hours, but the same effective results can be obtained with treatments shorter than 90 minutes and with a higher ozone concentration, preferably between 6 and 8 ppm. In order to achieve a higher ozone concentration, the ozonated water obtained in a first reactor of the ozone-production equipment can be made to pass through a second ozone-generating reactor, thus, the amount of ozone present in the ozonated water used in the treatment of the soil or medium at field capacity can be doubled.

The use of ozone in disinfecting soils implies a series of technical problems that had not been solved until now. In particular, an effective system for producing the amount of ozone necessary for treating the terrain in an economically-viable manner was not known. Moreover, due to the fact that the useful life of ozone is a few minutes, it is necessary for the ozone production to be performed with mobility, in other words, that the ozone can be produced in the application site and during the treatment. In relation to the aforementioned, in order to achieve a greater effectiveness of the disinfection treatment, it is preferable that the ozone-production equipment be small, being able to access the irrigation heads without difficulty.

In the method for disinfecting soils or other agricultural growing media which is described in this patent application, the ozone in gas form is thoroughly mixed with the irrigation water until the water is saturated with ozone gas, thereby enabling the effective transportation thereof to the deepest layers of the soil. Preferably, the water and ozone mixture takes place with ozone gas in the form of nano-bubbles. Thus, in the method of the present invention a much greater mobility of the ozone is achieved, thereby increasing the homogenisation in the water. As a result, the method of the present invention provides an effectiveness of the treatment which is much greater than if ozone gas were injected directly, while the implementation is much less complicated and expensive.

In the present invention, "other agricultural growing media" is understood as those substrates used in hydroponic agriculture, in other words, cultures wherein the roots grow in an artificial medium formed by different permeable materials with the ability to retain moisture and nutrients.

The method described in this document can be preferably used to disinfect soils in woody crops such as fruit, citrus or vines. In these particular embodiments of the invention, the disinfection method provides the following advantages:
  Increase in the amount of oxygen in the soil, favouring the development of the root system, in particular, of the crops aged by bad working practices.
  Cleaning of chemical residues.
  Additionally, the inoculation of formulations based on 11 strains of different microorganisms enables the microbial flora to be balanced with a diversity of living creatures that are beneficial for the crops;
  Increase in the quality of the crop, in particular the calibre of the fruit, and increase in production.

The ozone-production equipment used in the disinfection method described in the present invention can be moved to the treatment site and, furthermore, it enables the modification of parameters such as:
  the concentration of ozone produced, depending on the oxygen load,
  the use of more than one ozone-generating reactor, in particular 2 sequentially, in order to thereby increase the ozone content in the ozonated water,
  the production of ozone by weight, depending on the current intensity used,
  the application time of the ozonation treatment,
  the percentage of water/ozone mixture and the size of the gas bubbles in the mixture,
  the pressure and the flow rate of irrigation water in the outlet of the equipment,
  the equipment enables the regulation of the pH of the water directly from the treatment equipment (for example, by means of a regular venturi device for pH).

This versatility enables each treatment to be adapted to the specific conditions of the soil or medium to be treated, in particular, the structure of the soil and the type and degree of the infection to be treated, as well as it enabling the conditions of the treatment to be adapted to the quality of the irrigation water that is going to be used.

In preferred embodiments of the method of the present invention, the ozone-production equipment comprises two main portions: in one of them the ozone is produced starting from oxygen and, in the other, the ozone is injected into the irrigation water network, subsequently going to a mixing tank. Preferably, the mixing tank is pressurised with a pressure between 2.5 and 3.0 atm. Thus, a more homogeneous mixture of the ozone in the water is achieved.

In the method for disinfecting soils and agricultural growing media described in this patent application the use of AGR-60 ozonation equipment, with a working flow rate of 3000 L/h, or AGRZ-800, with a working flow rate between 10,000-80,000 L/h and able to treat crop surfaces of 5 Has is especially advantageous.

Additionally, in the method for disinfecting soils or agricultural growing media described in this document, 40 kVA light generators can be used. This causes a reduction in the electrical consumption and, consequently, a reduction in the environmental contamination produced by fuel consumption (diesel).

An additional problem related to the use of ozone to disinfect soils or media for agricultural use is the low solubility of the ozone in water, although this solubility is greater than that of oxygen, it is still complicated, like that of any gas mixed with a liquid.

In order to solve this technical problem and achieve the saturation of the irrigation water with ozone gas, the method for disinfecting soils or other agricultural media of the present invention comprises the use of a mixing tank, preferably pressurised with a pressure between 2.5 and 3.0 atm, wherein the size of the bubbles generated when the gas is injected into the irrigation water is decreased until the aforementioned nano-bubbles are achieved. Therefore, the load of ozone gas carried by each litre of water is much greater than that which could be reached until now, enabling the use of a smaller number of ozone-generating reactors, as well as a lesser electrical consumption and a decrease in the size of the equipment necessary for applying the treatment, enabling the mobility of the mentioned equipment.

In order to obtain the nano-bubbles of ozone, a recirculation of the water mixed with ozone through ceramic sieves must be achieved, preferably with a pressure of 2.5-3.0 atm, depending on the flow rate of irrigation water. For example, for a flow rate of 40,000 l, a pressure of 3 atm is needed in the mixer. This pressure and flow rate can be automatically regulated by means of an automatic pilot valve.

The use of ozone in low concentrations, in particular between 0.4 and less than 2 ppm, enables the water used for the treatment to be disinfected, given that the ozone does not act only as a deodorant and oxidant for the dissolved organic substances, but also as a disinfectant.

As mentioned earlier, ozone is an oxidising agent and a germicide. Consequently, it can be used for the oxidation of organic matter present in the water, creating odour and colour in the treated water. Ozone is used more and more as an oxidising agent due to the efficiency thereof, with a REDOX potential of 2.07 eV. Thanks to the oxidising potential thereof, ozone has the advantage of reducing the time normally needed for disinfection.

The use of this type of ozonated water contributes quality water to the crop, which is free of pathogens, but lacking disinfectant capacity in the soil, since the low ozone load is rapidly deactivated when it comes into contact with the organic matter present in the soil. Thus, the use of water with ozone at low concentrations (less than 2 ppm), whether it be for drip irrigation, such as misting or micro-spraying, contributes water free of pathogens, which enables the plants to grow in a medium that is favourable and septic for the crop. However, these conditions have a very brief persistence, for which reason this system must be irrigated in a practically continuous manner, which prevents the colonisation of beneficial microorganisms.

However, the method described in this patent application enables a soil or other agricultural growing medium to be disinfected by means of the treatment thereof with water containing a sufficiently high amount of dissolved ozone, in particular, containing an amount greater than or equal to 2 ppm. Therefore, the method of the present invention enables achieving, by means of punctual applications of the treatment, not only the disinfection of the irrigation water, but also of the ducts used and the soil or agricultural growing medium treated, since this method enables the ozonated water to arrive at the soil and penetrate deeply, maintaining the ozone load thereof and, therefore, the disinfectant power thereof.

The soil or medium to be treated must be in field capacity before performing the treatment with ozone. To do so, if necessary, water is previously applied to the soil or medium until field capacity is reached, an amount which will depend on the features and structure of the soil, for example, sand, clay; of the existing crop or the one to be planted; of the irrigation system used and the irrigation habits of the farmer.

The ozone in gas form has practically no mobility in the soil, whether the soil is compacted or aerated. Once the ozone has been mixed with the irrigation water it is easily extended over a soil in field capacity, reaching the ends of the irrigation bulb, in the case of emitters, or the deepest layers, in the case of spraying, quickly.

The useful life of ozone at a water temperature of 15° C. is 30 minutes, and at 25° C. it is 15 minutes, for which reason we must make the ozone produced run through the tubes to the emitter and move through the terrain in field capacity to the outside of the irrigation bulb before it degrades and transforms into oxygen. The inventors have observed that, when applying the method of the present invention, the time necessary to drain water with ozone in a hydroponic crop is less than that useful life.

In preferred embodiments of the present invention, the treatment with ozone takes place during a period of time less than 2 hours, in this manner guaranteeing that the water with disinfectant load reaches the limits of the irrigation bulb, achieving the disinfection of the existing microorganisms.

Taking into account that the disinfection with ozone does not generate resistances due to the mode of action, the method of the present invention enables the total disinfection of the soil or medium treated to be achieved. Once the treatment with ozone has ended, the method comprises inoculating at least one species of beneficial microorganism which recolonises that empty space and thereby prevents access thereto for opportunistic pathogens. Preferably, these beneficial microorganisms are selected from the group consisting of *Trichodermas, Bacillus, Azotobacter, Pseudomonas* and any one combination of the preceding.

In preferred embodiments, the method for disinfecting a soil or agricultural growing medium comprises inoculating 11 different strains of microorganisms. The formulas of different strains recolonise the microbial flora in less time and with a better guarantee than the formulas with a single strain which are usually used. In an especially preferred manner, the method for disinfecting a soil or agricultural growing medium described in this document comprises inoculating the following microorganisms: *Bacillus pumilus, Bacillus licheniformis, Bacillus megaterium, Bacillus subtilis, Bacillus popilliae, Azotobacter vinelandii, Pseudomonas fluorescens, Saccharomyces, Glomus intraradices, Trichoderma harzianum, Rhizobium* spp and *Paecilomyces lilacinus.*

The inoculation with beneficial microorganisms takes place at least 30 min after finishing the treatment with ozone. The minimum period of 30 min enables the degradation of the residual ozone before the inoculation. Moreover, it is preferred that the inoculation takes place in a period no longer than 48 hours, more preferably, no longer than 24 hours, from the application of the treatment with ozone. In this manner, it can prevent the treated area from being exposed to a quick inlet of opportunist pathogens which can be more aggressive and dangerous than before the disinfection, given that there will be no beneficial microorganisms which neutralise the effects thereof.

The application of water in the different steps of the method described in this patent application can be performed by any method known by a person with skill in the art, preferably by means of localised irrigation or spraying. In particular, it is preferable for the input of water with ozone to take place by means of drip irrigation on the soil, since in this manner a more effective disinfecting action is produced, eliminating bacteria, fungi, viruses and nematodes initially present in the soil or medium to be treated. Preferably, the beneficial microorganisms are applied in the disinfected bulb wherein the root system of the crop is located. The mixture of microorganisms adheres to the root system, protecting and colonising the disinfected, or in other words, free space. Additionally, they activate the natural defences of the plants, and degrade the organic matter existing in the soil, converting it into humic and fulvic acids that are more easily assimilated by the crop. For this reason, it is particularly advantageous to use the mixture of 11 different strains of beneficial microorganisms described in this document.

In other preferred embodiments, the inoculation with microorganisms takes place by means of an injector located in the ozonation equipment.

The effectiveness of the disinfection of the pathogen is influenced by the contact time, the ozone concentration, the temperature of the water used as a mobility pathway, the pH and the dissolved organic and inorganic substances. Thus, we can affirm that the power of the disinfection increases with a low pH (between 5.0 and 7.5; more preferably between 5.0 and 7.0; the optimal pH being between 5.6 and 6.5) and with a low water temperature. The lower the temperature the better the dissolution of the ozone in the water, an interval between 8° C. and 25° C. being preferable, more preferably between 10° C. and 20° C., the optimal temperature being 15° C.

In other preferred embodiments, the water used in the method described in this patent application, in particular, the irrigation water used in the ozonation step, is devoid of additives such as mineral fertilisers or organic matter. In the method of the present invention, the treatment with ozonated water is more effective when the levels of organic matter in the tubes are low (preferably, REDOX values of the water between 600 mV and 1100 mV must be reached), the temperature of the soil and water are also low (preferably, between 10 and 20° C.) and the pH is preferably between 5.0 and 7.0.

In other preferred embodiments, the method for disinfecting soils or other media for agricultural growing is performed punctually, also being able to be performed before or during the growing. It is also possible to perform repeated ozone treatments, since this treatment does not generate residues that are harmful for the crop.

Thus, the use of ozone as a disinfectant in the method for disinfecting soils or other types of media for agricultural growing of the present invention has several important advantages. On the one hand, due to the oxidising properties thereof, ozone is considered as one of the quickest and most effective microbicidal agents known. Additionally, the use of ozone does not contaminate the soil or the medium treated, nor does it leave harmful residues. On the contrary, since the degradation product thereof is oxygen, the use of ozone favours the root development and the plant growth.

However, ozone generally degrades very quickly which makes it enormously difficult to perform the treatments based on this compound. For example, in conditions of water without organic matter, a pH of 7 and a water temperature of 15° C., the degradation of the ozone into oxygen is produced about 30 minutes from when it is generated. For this reason, it is especially advantageous that the method of the present invention enables the production of the necessary amount of ozone when and wherein the disinfecting action thereof is needed.

The method described in this patent application can be applied to soils or other media without crops in production. In these cases, the method preferably comprises the following steps:
preparing the soil or medium for planting;
obtaining the soil or medium at their field capacity;
treating the soil or medium at the field capacity of the previous step with ozonated water containing at least 2 ppm of ozone, wherein the ozonated water is prepared in situ with ozone-production equipment connected to the water supply with a pH between 5.0 and 7.5, preferably a pH between 5.0 and 7.0;
allowing a minimum period of 30 min to pass after the treatment with ozone, preferably between 30 min and 48 hours;
inoculating the disinfected soil or agricultural medium with at least one species of beneficial microorganism, preferably with a mixture of 11 different strains of microorganisms; and
planting the plant to be grown.

In an especially preferred manner, the method for disinfecting a soil or agricultural growing medium described in this document comprises inoculating the following microorganisms: *Bacillus pumilus, Bacillus licheniformis, Bacillus megaterium, Bacillus subtilis, Bacillus popilliae, Azotobacter vinelandii, Pseudomonas fluorescens, Saccharomyces, Glomus intraradices, Trichoderma harzianum, Rhizobium* spp and *Paecilomyces lilacinus*.

The step of preparing the soil or medium for planting can comprise performing the tasks of decompacting and forming ridges or small plateaus, installing the irrigation network and, if necessary, installing mulching if necessary.

Preferably, the treatment with ozonated water comprised in the method for disinfecting soils or other agricultural growing media which is described in this patent application comprises the application, by means of the irrigation network in the disinfected bulb, of beneficial microorganisms which recolonise the growing soil and prevent recolonisation by pathogens.

The planting can be performed with the usual systems, including the placement of tunnels or mulching which are needed for the normal development of the crop.

The method of the present invention has shown that it is effective for disinfecting soils against phytopathogenic fungi such as, for example *Sclerotinia* sp, *Fusarium oxysporum* and *Phytophthora citrophthora*. In particular, in assays performed, a disinfection of 100% against the aforementioned phytopathogenic fungi was obtained.

Additionally, this disinfection method is also effective against populations of pathogenic mesophilic bacteria such as, for example, *Erwinia amylovora* and *Clavibacter michiganensis*. In the assays performed with respect to these bacteria, a mortality of less than 50% was obtained after a first application of ozonated water. Subsequently, after a second application, a reduction of at least 50% was maintained.

As a result of the reduction of the microorganism populations achieved with the disinfection method of the present invention, an increase is achieved in the plant development of the plants grown in said soil or medium.

Thus, the method of the present invention enables ozone to be used as a disinfectant of the soil or medium, since it enables the necessary amount of ozone to be effectively generated when and wherein it is needed. Therefore, this method provides a viable alternative to the disinfection of agricultural soils, as a step before the planting of the crop, preventing the use of phytosanitary products, the contamination and accumulation of residues in the soil and plant. This is due to the fact that ozone has a strong oxidising power, eliminating the microorganisms since the release of oxygen free radicals in large amounts eliminates the microbes from the soil.

Alternatively, the method described in this patent application can be applied to soils or other media with crops in production, both leafy and woody crops (fruit, citrus, vines, etc). In these cases, the method preferably comprises the following steps:

obtaining the soil or medium at their field capacity;
treating the soil or medium of the previous step with ozonated water containing at least 2 ppm of ozone, wherein the ozonated water is prepared in situ with ozone-production equipment connected to the water supply with a pH between 5.0 and 7.5, preferably a pH between 5.0 and 7.0;
allowing a minimum period of 30 min to pass after the treatment with ozone, preferably between 30 min and 48 hours;
inoculating the disinfected soil or agricultural medium with at least one species of beneficial microorganism, preferably with a mixture of 11 different strains of microorganisms.

In an especially preferred manner, the method for disinfecting a soil or agricultural growing medium described in this document comprises inoculating the following microorganisms: *Bacillus pumilus*, *Bacillus licheniformis*, *Bacillus megaterium*, *Bacillus subtilis*, *Bacillus popilliae*, *Azotobacter vinelandii*, *Pseudomonas fluorescens*, *Saccharomyces*, *Glomus intraradices*, *Trichoderma harzianum*, *Rhizobium* spp and *Paecilomyces lilacinus*.

The method described in this patent application enables soils or other agricultural growing media to be disinfected instantaneously, without leaving harmful residues since the only by-product resulting from the degradation of ozone in the soil is oxygen, which is very beneficial for the root development and the planting of beneficial microorganisms.

Both in the use of chemical disinfections as well as in solarisation techniques, the waiting time after the disinfection necessary for it to be effective is between 20 and 60 days. Advantageously, the disinfection method of the present invention enables the disinfection of the soil with the crop planted, in other words, it enables ozone to be applied to the soil or medium infested with pathogens and with the crop in production, without leaving any type of toxic residues or being able to be recorded in the analysis of the collected product. The inoculation, preferably between 30 minutes and 48 hours after the treatment with ozone, of beneficial microorganisms will be responsible for regenerating the affected root system.

It is also advantageous that if a high infection of pathogens is produced during the growing, the method of the present invention can be performed several times, since residues are not generated, nor does it negatively affect the vegetation. Furthermore, it is also possible to perform treatments with ozone (several applications of ozone) before proceeding to the inoculation with the beneficial microorganisms.

Additionally, the disinfection method described in this patent application is highly versatile, since it can be applied before or after the planting, after performing a chemical disinfection by another known method or without having performed any type of prior disinfection.

BRIEF DESCRIPTION OF THE FIGURES

FIG. 5: Image showing the state of the tomato plants after the first application of example 1: FIG. 5a: control; FIG. 5b: treatment with ozone.

FIG. 6: Image showing the state of the tomato plants after the second application of example 1. FIG. 6a: control; FIG. 6b: treatment with ozone.

EXAMPLES

Example 1: Effectiveness of the Treatment with Ozone in the Disinfection of Soils without Crops The general objective of the study was to evaluate the effectiveness of the use of ozone as a strategy in the disinfection of soil. In particular, the effect of the disinfection method on tomato plants was to be studied, as well as relating the oxidising power of the ozone with the elimination of pathogens at different depths.

In order to achieve the aforementioned objectives, soil without crops was infected with the phytopathogenic species Sclerotinia, Fusarium, Erwinia, Phytophthora and Clavibacter. The assay was performed in Lorca (Murcia). It took place in open air in bins with soil without crops and wherein tomatoes, peppers and melons had been grown previously. After performing the first application of the method of the present invention, tomato plants, Lycopersicum esculentum, were transplanted, the response of the plants to the treatments being evaluated.

The treatments tested were: T0 (control) and T1 (ozone). After the application of the method two consecutive times, the inoculation of the following beneficial microorganisms (mixture called "microorganism formula (1)") was performed: Trichodermas ($4 \times 10^8$ UFC), Bacillus ($1.5 \times 10^8$ UFC), Azotobacter ($1.5 \times 10^8$ UFC) and Pseudomonas ($1.5 \times 10^8$ UFC).

The microbiological content of the soil was evaluated at different depths: 20, 40 and 60 cm., before and after the applications.

1.1 Assay Protocol

Containers were installed with a known volume of 1000 l ($1 \times 1 \times 1$ m) in field. Moreover, a medium proceeding from a greenhouse with melons, peppers and tomatoes having been grown there previously was selected and homogenised. Subsequently, the containers were filled with this medium.

In the laboratory, the following species were cultivated in vitro:

Phytopathogenic bacteria: Erwinia amylovora and Clavibacter michiganensis

Phytopathogenic fungi: Sclerotinia sp, Fusarium oxysporum and Phytophthora citrophthora Each microorganism was grown in liquid medium until reaching a concentration of $10^8$ ufc/ml. For each of the bins, 1 litre of microbial solution was prepared.

Then the pathogenic microorganisms were inoculated in the medium, periodic irrigations were performed until reaching the capacity of the medium, samples were taken at different depths (20 cm, 40 cm and 60 cm) and the phytopathogens were counted in said samples, in order to verify the permanence and presence of phytopathogens in the soil.

A first application of the disinfection method with ozone was performed. To do so, the ozonation equipment was inserted into the irrigation system and the parameters of said equipment were adjusted in order to achieve ozonated water with at least 2 ppm of dissolved ozone. Subsequently, the soil was left to rest for 30 min and the tomato plants, Lycopersicum esculentum, were transplanted. Subsequently, a second application of the disinfection method with ozone was performed in the same conditions indicated previously and, after letting the treated soil rest for 30 min, the microorganism formula (1) was inoculated.

Figure 2A:
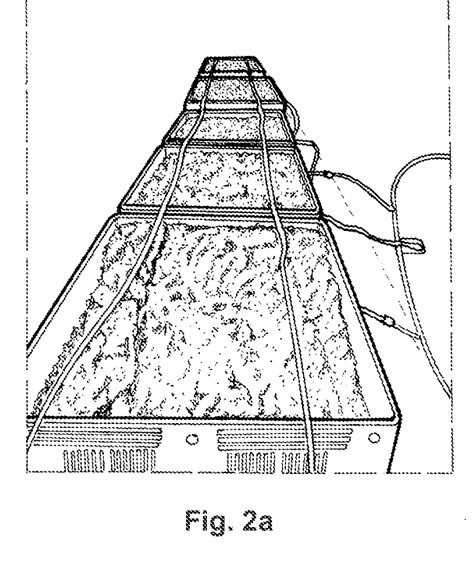
FIG. 2a: Image showing the containers with medium used in example 1.
Figure 2B:
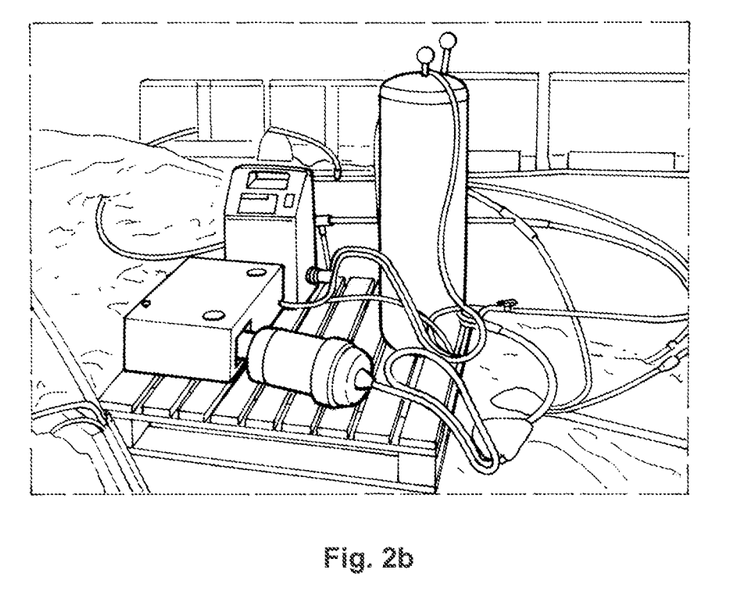
FIG. 2b: Image showing the system used in example 1 in order to perform the disinfection of a medium according to the method of the present invention.

FIG. 2a shows the placement of the containers in the field, while FIG. 2b shows the assembly made for inserting the ozonation equipment into the irrigation system.

In order to analyse the effect of the treatment on the disinfection of the soil, samples were taken at different depths (20 cm, 40 cm and 60 cm) and on different dates, and the microbial load in each of the samples was analysed.

Afterwards, as mentioned earlier, once the first disinfection was finished, tomato seedlings were transplanted into the bins in order to evaluate the "residual effect" of the treatment. Subsequently, the study of the plant development of the plants was performed.

1.2 Treatments

The treatments, applications and sampling are referred to in the following table:

| Code | Description | Application 1 | Sampling 1.1 | Sampling 1.2 |
|---|---|---|---|---|
| T0 | Control | | 12-Sep | 16-Sep |
| T1 | Ozone | 15-Sep | 12-Sep | 16-Sep |

| Code | Description | Application 2 | Sampling 2.1 | Sampling 2.2 | Sampling 2.3 |
|---|---|---|---|---|---|
| T0 | Control | | 14-Oct | 17-Oct | 14-Nov |
| T1 | Ozone | 16-Oct | 14-Oct | 17-Oct | 14-Nov |

After the first application of the disinfection method, on 19 Sep. 2014, 2 tomato plants were transplanted per container. The residual effect of the ozone was evaluated.

1.3 Experimental Size and Design

The control treatment corresponds to container No. 1. Given that there is only one repetition, during the samplings, 3 subsamples were taken.

TABLE 2

Outline of the experimental design

| Code | Description | Repetitions | Container Code |
|---|---|---|---|
| T0 | Control | 3 | 1, 2, 3 |
| T1 | Ozone (>2 ppm) | 3 | 4, 5, 6 |

1.4 Parameters Evaluated

Throughout the assay, the parameters evaluated were:

Flow rate and ppm ozone at the outlet.

Microbial evaluation of the soil (t=0; t=7 days and t=30 days).

Relationship of the depth with the possible fungicidal effect.

Having established the tomato plants, it was evaluated if the treatments caused phytotoxicity.

The parameters that will be observed in the crop will be the appearance of necrosis and burning on leaves and fruits.

Plant development of the crop.

The effect of the treatments (ozone, control) and the evaluation thereof were determined by means of the Student test in the SPSS statistical packet. The test determines whether the measurements produced by the experiments are significantly different with a level of reliability ($P > 0.05$). The results are shown by means of bar diagrams. In the results table, it is shown if there were significant differences (different letter) or if there is no evidence of differences between the treatments (same letter).

1.5. Results 1.5.1 Flow Rate and ppm Ozone at the Outlet

During the first application, the data collected is shown in the following table:

TABLE 3

Ozone readings

| Time (minutes) | Equipment involved | Description/Observations |
|---|---|---|
| 0-120 | Irrigation | Water saturation |
| 15-20 | Ozone equipment Drip irrigation | Verification on 4 occasions of the analysis in order to determine the grams of ozone per litre of water. 2 ppm. Minimum level for a good disinfection |

TABLE 3-continued

Ozone readings

| Time (minutes) | Equipment involved | Description/Observations |
|---|---|---|
| 15 | Reading | 2 ppm |
| 55 | Reading | 2.3 ppm |
| 65 | Reading | 2.89 ppm |
| 115 | Reading | 4.49 ppm in the direct outlet of the pump 3.92 ppm in the dripper |

1.5.2. Evaluation of the Microbial Population after Application 1

In this section the data obtained is described. As explained in the assay protocol, soil samples were taken at different depths (20 cm, 40 cm and 60 cm) and quality controls were performed quantifying the number of pathogenic fungi and bacteria present.

A. Pathogenic Fungi

Figure 3A:
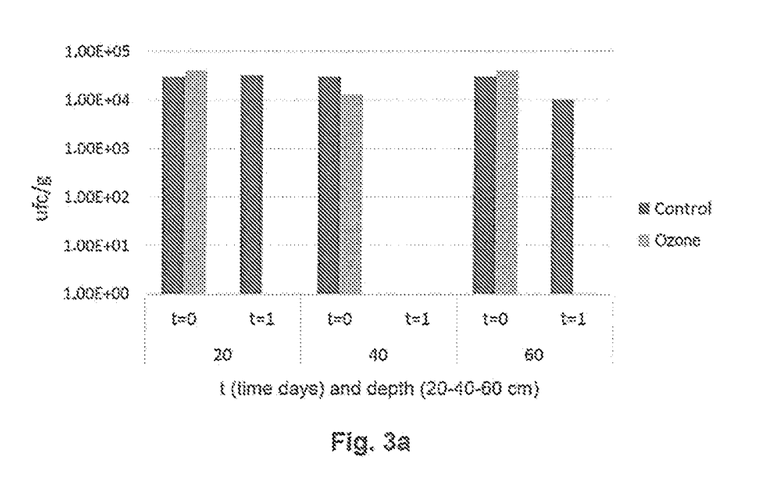
FIG. 3a: Graph showing the survival of phytopathogenic fungi after application 1 of example 1. The amount of fungi present in the medium at time zero (t=0) and 24 hours after the application (t=1), at depths of 20 cm, 40 cm and 60 cm, is analysed.

Prior to the incorporation of the treatments and 24 hours after the application, the survival of pathogenic fungi was evaluated. Having analysed the data by treatment (see FIG. 3a), we found that:

In the control treatment: the microbial load was similar before and after at all the depths tested, except for 40 cm, wherein washing was produced.

The ozone application caused a 100% reduction at depths of 20 and 60 cm.

B. Pathogenic Bacteria

Figure 3B:
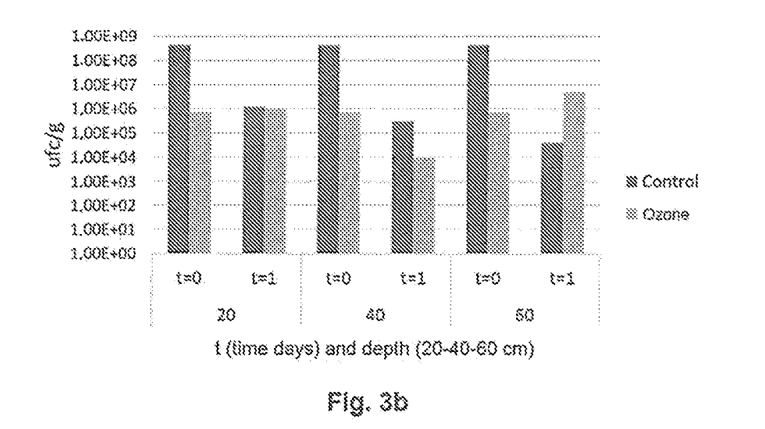
FIG. 3b: Graph showing the survival of phytopathogenic bacteria after application 1 of example 1. The amount of bacteria present in the medium at time zero (t=0) and 24 hours after the application (t=1), at depths of 20 cm, 40 cm and 60 cm, is analysed.

At each of the depths tested (20 cm, 40 cm and 60 cm), both treatments reduced the populations of bacteria present in the soil (see FIG. 3b). At all the depths tested (except for 60 cm), the populations of pathogenic bacteria were less than the control, this reduction being less than 50%.

1.5.3. Evaluation of the Microbial Population after Application 2

A. Pathogenic Fungi

Figure 4A:
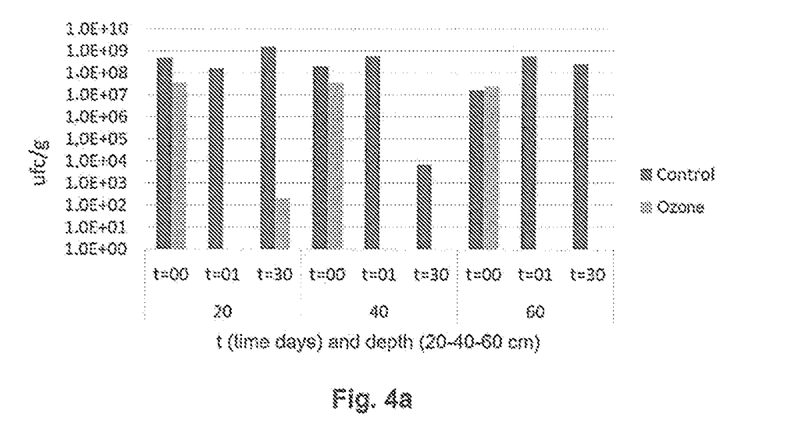
FIG. 4a: Graph showing the survival of phytopathogenic fungi after application 2 of example 1. The amount of fungi present in the medium at time zero (t=0), 1 day (t=1) and 30 days (t=30) after the application, at depths of 20 cm, 40 cm and 60 cm, is analysed.

As shown in FIG. 4a, the application of ozone reduced the pathogenic fungi by 100% at depths of 40 and 60 cm, maintaining the effectiveness of both products and prolonging the effect for 30 days at a depth of 20 cm, the treatment with ozone reduced the population by 100%, with traces of fungi appearing a month later, possibly due to contamination of the soil from environmental factors.

B. Pathogenic Bacteria

Figure 4B:
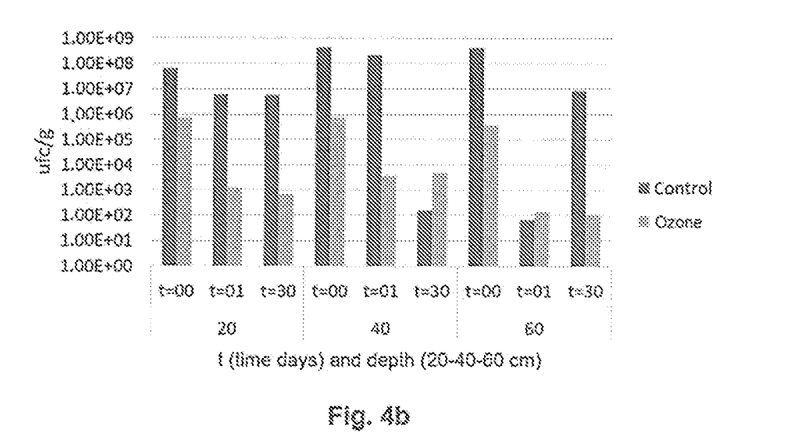
FIG. 4b: Graph showing the survival of phytopathogenic bacteria after application 2 of example 1. The amount of fungi present in the medium at time zero (t=0), 1 day (t=1) and 30 days (t=30) after the application, at depths of 20 cm, 40 cm and 60 cm, is analysed.

The study of the data (see FIG. 4b) shows the disinfecting power of the ozone, although the reduction was not complete. Given the reproduction speed of the bacteria, it is estimated that after the residual effect of the products disappear completely, populations similar to the control will be reached.

1.6. Phytoxicity in Tomato Plants

Figure 5A:
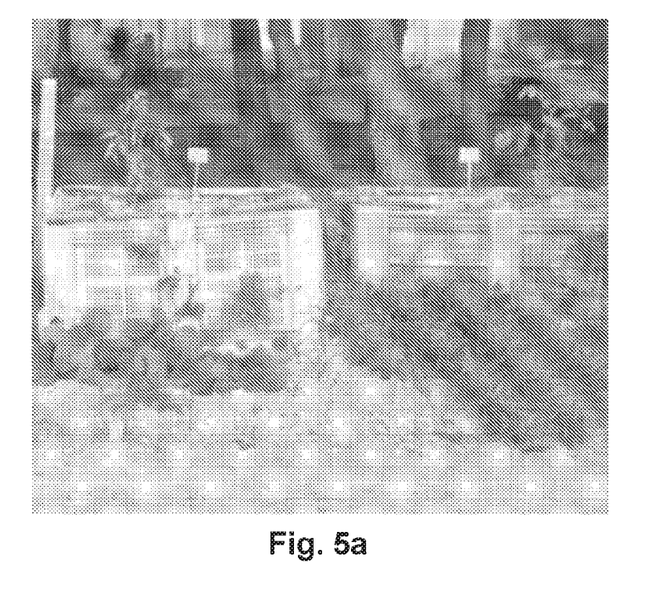
Figure 5B:
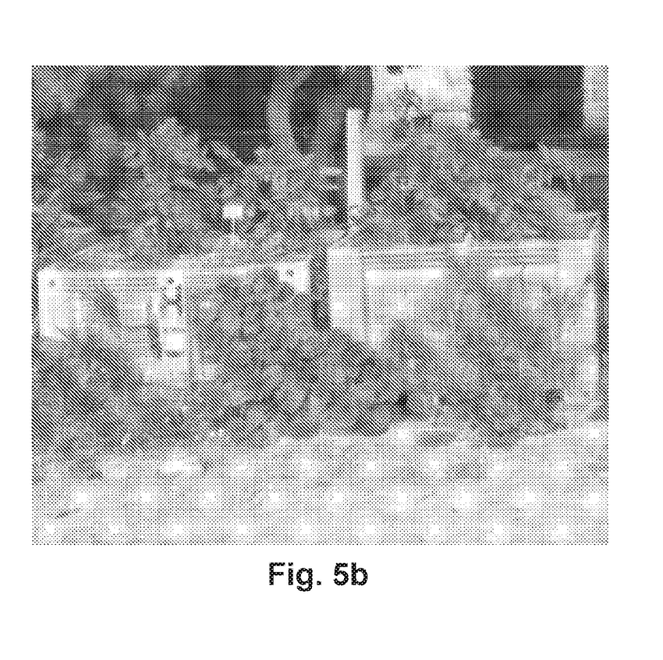

After the first application of the treatment with ozone, 2 tomato plants were transplanted into each of the containers. The growth of the plants was evaluated for three months, ending the analysis of this parameter on 2 January due to frost in the area (see FIGS. 5a and 5b).

Figure 6A:
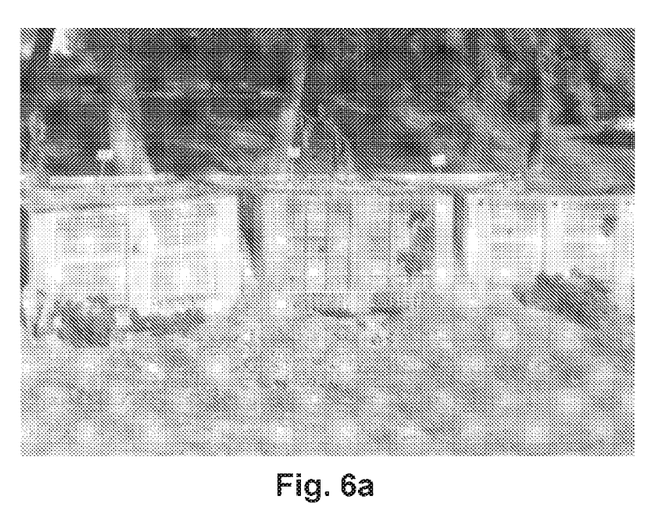
Figure 6B:
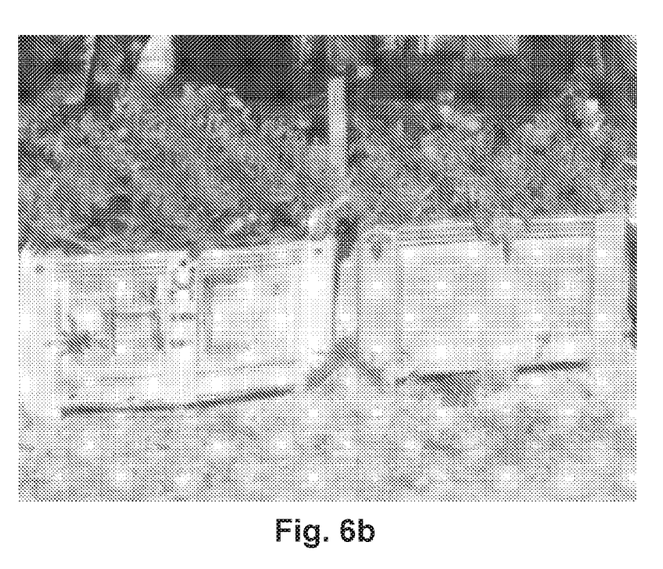

The growth in plants wherein the treatment with ozone had been applied showed vigorous plant development, due to the decrease in pathogenic microorganisms; while in control plants, the development thereof was medium-low. Two weeks after the second application, the control plants died from the infection (see FIGS. 6a and 6b).

1.7. Conclusions

The results obtained demonstrated that the disinfection level of the ozone was 100% against the phytopathogenic fungi tested. Additionally, the populations of pathogenic mesophilic bacteria decreased in number after the application of the disinfectant, with a mortality less than 50% after the first application. During the second application, the reduction of 50% was maintained, except for what was observed at a depth of 60 cm, wherein the reduction reached 60%.

Furthermore, in the samples treated with ozone, the plant development of the tomato plants was vigorous due to the reduction of the populations of microorganisms, meanwhile, the tomato plants grown in control containers showed a low-medium growth and ended up dying due to the infection by pathogens.

In addition, after the first application, tomato plants were transplanted into each of the repetitions and it was evaluated whether the application of ozone caused phytotoxicity. Three months after the transplant, plants treated with ozone exhibited normal growth and plant development, while the control plants died as a consequence of the attack of pathogens present in the soil.

Example 2: Disinfection of Nematodes in Padrón Peppers

The assay was performed in a property with Padrón peppers in the month of May 2015 which is significantly affected by nematodes and the property intends to start planting since the production has already been considered lost. On a 500 m² surface of a greenhouse, with a water consumption of 3000 l/h, the disinfection with ozone was performed at a dose of 6 ppm, revising with the REDOX readings that a reading of 1000 mV is obtained in the farthest drip emitters, starting from a value of 185 mV in the irrigation water without ozone.

When the treatment ends, the inoculation of the microorganism formula (1) is performed (see example 1). Seven days after performing the treatment, samples of earth are taken to see the level of nematode infestation, observing a decrease of 90% of the population.

In particular, after the disinfection through ozonated irrigation in a Padrón pepper crop affected by nematodes (*Meloidogyne*) in full production, the following results were obtained:

Analytics before the disinfection: *Meloidogyne* sp. 88 juveniles/100 cc soil

Analytics after the disinfection: *Meloidogyne* sp. 8 juveniles/1 cc soil.

The treated portion of the property recovered from the damage and continued to produce until the date foreseen for the start thereof.

Example 3: Disinfection of Nematodes in Citrus Crops (Lemon Trees). Effect of Ozonation and Inoculation with Beneficial Microorganisms in the Control of Phytopathogenic Nematodes in Soil The present assay in citrus plants was performed in a parcel of land with a high index of nematode infection, during the months of May and September 2015. The effect of two ozone applications and a final application of a mixture of microorganisms (microorganism formula (2)) made of: *Bacillus* ($1.5 \times 10^8$ UFC), *Azotobacter* ($1.5 \times 10^8$ UFC) and *Pseudomonas* ($1.5 \times 10^8$ UFC) was evaluated.

The parameters studied were: evolution of the phytopathogenic nematode population, evolution of the fungal population and after the application of microorganism formula (2), a count of the number of bacteria in the soil was performed. The results show that the application of the ozone together with beneficial microorganisms significantly reduced the population of phytopathogenic nematodes in the soil.

An objective of this assay was to evaluate the action of ozone and beneficial microorganisms in the control of phytopathogenic nematodes in citrus plants.

3.1. Material and Methods

Figure 7:
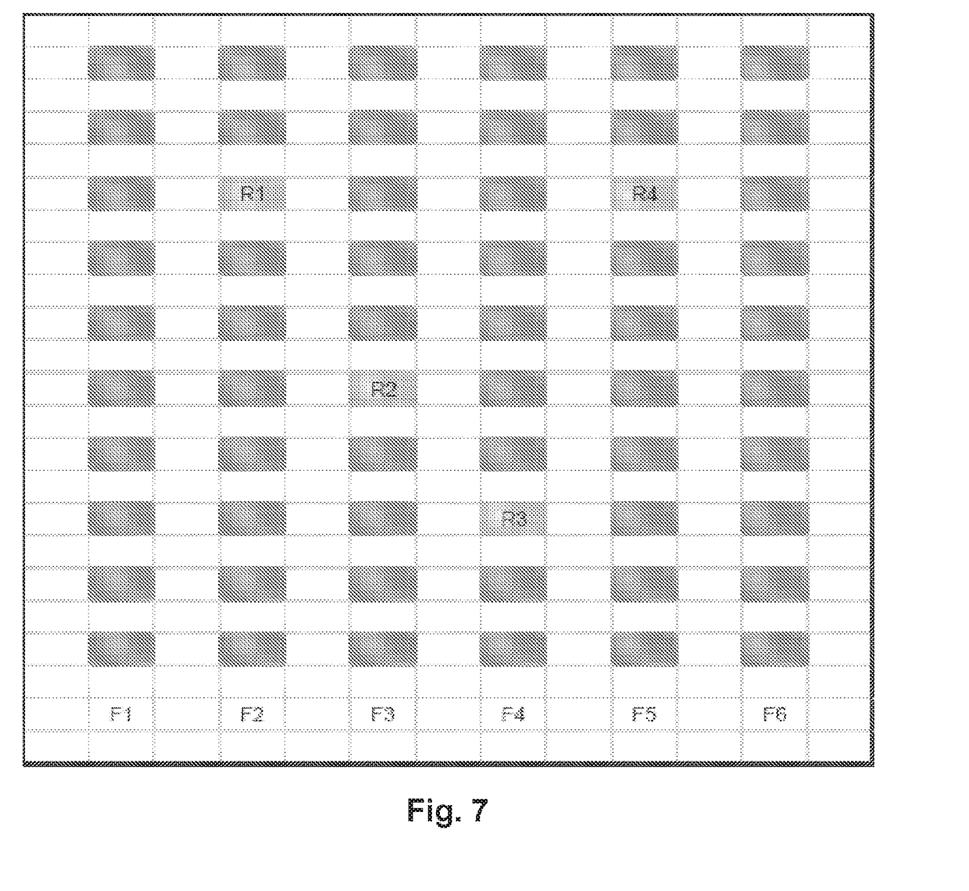
FIG. 7: Sampling points collected in example 3.
Figure 8:
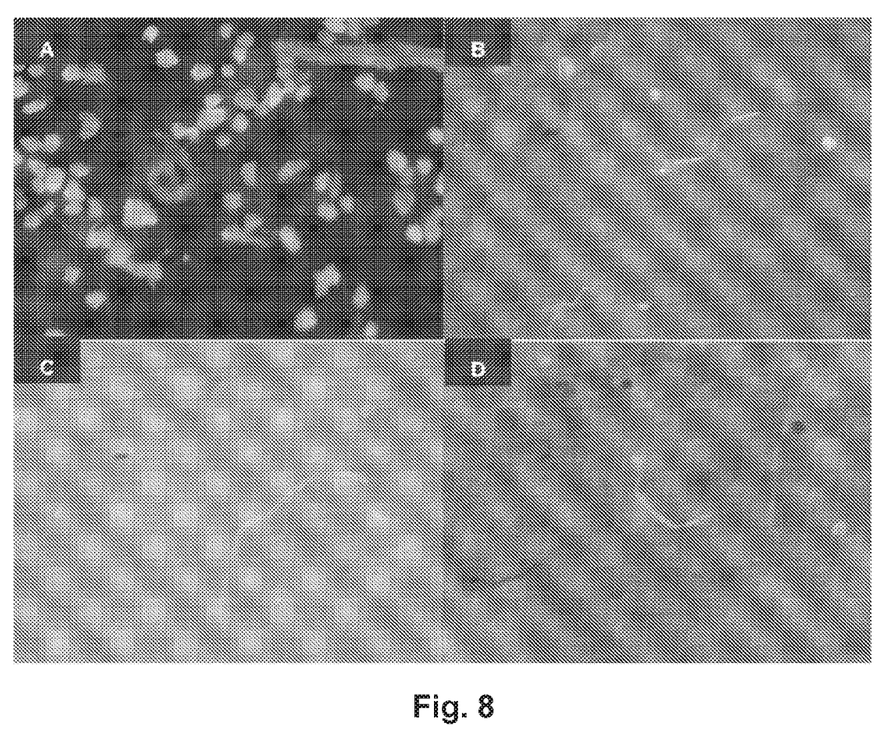
FIG. 8: Images showing: (A) soil sample under a microscope; (B), (C) and (D) detail of nematodes.

On a parcel of land with a high infection by nematodes of the genus *Pratylenchus* sp, 4 repetitions were selected. FIG. 7 shows the sampling points gathered.

The application date of the products was:

Ozone: applied at a concentration of 5-6 ppm. Applications: 21 and 27 May.

Microorganism formula (2) (Bionema Plus): A single application of a dose of 20 l/ha took place on 4 July.

TABLE 1

| Samplings | | |
|---|---|---|
| Sampling | Description of the application | Date |
| Sampling 1 | Before application | 20-May |
| Sampling 2 | After application 1 of Ozone | 21-May |
| Sampling 3 | After application 2 of Ozone | 28-May |
| Sampling 4 | After application of Bionema Plus | 23-Sep |

3.2. Conclusions

The results have shown that the application of the ozone and the microorganism formula (2) significantly reduced the population of phytopathogenic nematodes, decreasing from 50 nem/g to 0.2 nem/g, the population being practically non-existent.

Example 4: Evolution of Nematodes in the Soil after Treatment with Ozone and Inoculation of Microorganisms This assay was performed in T. M. Benifaió (Valencia), in clay-loam terrain. The treatments were performed at the end of a crop of vegetables, before performing the new planting of vegetables such as cucumbers, tomatoes, peppers.

The terrain was notable for the high content of nematode infection thereof, severely affecting the production of the crop.

The method for disinfecting soils which is described in this patent application was applied, wherein the treatment with ozonated irrigation water (5.5 ppm of ozone) was performed for 2 hours, and the inoculation took place by means of the application of the colonising microorganism formula (1) (see example 1) 24 hours after performing the disinfection with ozone.

Figure 9:
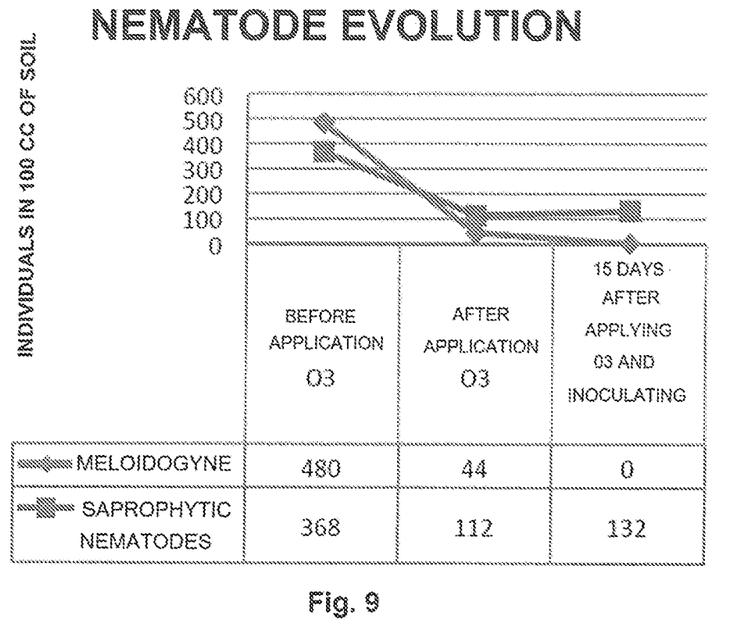
FIG. 9: Graph showing the evolution of the nematode population in the soil after the treatment with ozone and after the inoculation of microorganisms obtained in example 5.

As can be observed in FIG. 9, before applying the treatment the soil sample taken had 480 juveniles/100 cc of earth. After performing the treatment with ozone, the presence of juveniles was reduced to 44/100 cc of earth and 15 days after performing the inoculation with the microorganism formula (1), the sample analysed had 1 juvenile/100 cc of earth.

These results show a considerable decrease in the percentage of nematodes. Furthermore, an increase can also be seen in the amount of saprophytes in 20 units/100 cc of earth.

The different assays performed show that, both in bare terrain as well as terrain with crops in production, the best results are obtained by combining the punctual treatment with ozone (at least 2 ppm) in irrigation water, followed by the inoculation with beneficial microorganisms.

The invention claimed is:

1. A method for disinfecting soils or other agricultural growing media, comprising the following steps:
   obtaining a soil or other agricultural growing medium at their field capacity;
   treating the soil or medium at the field capacity of the previous step with ozonated water containing at least 2 ppm of ozone, wherein the ozonated water is prepared in situ with ozone-production equipment connected to the water supply with a pH between 5.6 and 6.5;
   allowing a minimum period of 30 min to pass after the treatment with ozone; and
   inoculating the disinfected soil or agricultural medium with at least one species of beneficial microorganism.

2. The method for disinfecting according to claim 1, wherein a period of between 30 min and 48 hours is allowed to pass between the treatment of the soil or medium with the ozonated water and the inoculation with at least one species of beneficial microorganism.

3. The method for disinfecting according to claim 1, wherein the content of ozone dissolved in the ozonated water is between 5 and 6 ppm.

4. The method for disinfecting according to claim 1, wherein the treatment with ozonated water is performed for a period of time between 1 h 30 min and 2 hours.

5. The method for disinfecting according to claim 1, wherein the content of ozone dissolved in the ozonated water is between 6 and 8 ppm, and the treatment of the soil or medium with this ozonated water is performed for a period of time less than 90 min.

6. The method for disinfecting according to claim 1, wherein the ozonated water prepared in situ contains nanobubbles of ozone obtained in a mixing tank pressurised at a pressure between 2.5 and 3.0 atm.

7. The method for disinfecting according to claim 1, wherein the beneficial microorganism is selected from the group consisting of *Trichodermas, Bacillus, Azotobacter, Pseudomonas* and any one combination thereof.

8. The method for disinfecting according to claim 1, wherein the disinfected soil or agricultural medium is treated with 11 different strains of microorganisms.

9. The method for disinfecting according to claim 1, wherein the water is applied by localised irrigation.

10. The method for disinfecting according to claim 1, wherein the soil or medium does not have a crop in production, and the method comprises the following steps:
    preparing the soil or medium for planting;
    obtaining the soil or medium at their field capacity;
    treating the soil or medium at the field capacity of the previous step with ozonated water containing at least 2 ppm of ozone, wherein the ozonated water is prepared in situ with ozone-production equipment connected to the water supply with a pH between 5.6 and 6.5;
    allowing a minimum period of 30 min to pass after the treatment with ozone;
    inoculating the disinfected soil or agricultural medium with at least one species of beneficial microorganism; and
    planting the plant to be grown.

11. The method for disinfecting according to claim 1, wherein the soil or medium has a crop in production, and the method comprises the following steps:
    obtaining the soil or medium at their field capacity;
    treating the soil or medium of the previous step with ozonated water containing at least 2 ppm of ozone, wherein the ozonated water is prepared in situ with ozone-production equipment connected to the water supply with a pH between 15.6 and 6.5;

allowing a minimum period of 30 min to pass after the treatment with ozone; and inoculating the disinfected soil or agricultural medium with at least one species of beneficial microorganism.

* * * * *

UNITED STATES PATENT AND TRADEMARK OFFICE
CERTIFICATE OF CORRECTION

PATENT NO. : 11,633,512 B2
APPLICATION NO. : 16/628843
DATED : April 25, 2023
INVENTOR(S) : Emilio Jesús Villanueva Decodes It is certified that error appears in the above-identified patent and that said Letters Patent is hereby corrected as shown below:

In the Claims

Column 17, Line 3, Claim 11, delete "15.6" and insert -- 5.6 --

Signed and Sealed this
Thirteenth Day of June, 2023

Katherine Kelly Vidal
*Director of the United States Patent and Trademark Office*